United States Patent
Cho et al.

(10) Patent No.: US 10,465,168 B2
(45) Date of Patent: Nov. 5, 2019

(54) PARTICLE FILTERING DEVICE AND METHOD

(71) Applicant: UNIST ACADEMY-INDUSTRY RESEARCH CORPORATION, Ulsan (KR)

(72) Inventors: Yoon-Kyoung Cho, Ulsan (KR); Tae-Hyeong Kim, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 117 days.

(21) Appl. No.: 14/780,002

(22) PCT Filed: Apr. 30, 2015

(86) PCT No.: PCT/KR2015/004422
§ 371 (c)(1),
(2) Date: Sep. 25, 2015

(87) PCT Pub. No.: WO2016/080609
PCT Pub. Date: May 26, 2016

(65) Prior Publication Data
US 2017/0247661 A1  Aug. 31, 2017

(30) Foreign Application Priority Data
Nov. 20, 2014 (KR) .................. 10-2014-0162937
Apr. 28, 2015 (KR) .................. 10-2015-0059830

(51) Int. Cl.
*C12N 5/09* (2010.01)
*C12M 1/00* (2006.01)
*C12M 1/26* (2006.01)

(52) U.S. Cl.
CPC .......... *C12N 5/0694* (2013.01); *C12M 23/02* (2013.01); *C12M 33/14* (2013.01); *C12M 47/02* (2013.01); *C12M 47/04* (2013.01)

(58) Field of Classification Search
CPC ......... B01L 3/502707; B01L 3/502753; B01L 2300/16; B01L 2300/069; B01L 2200/12;
(Continued)

(56) References Cited

U.S. PATENT DOCUMENTS 4,013,072 A    3/1977  Jess
4,731,260 A    3/1988  Balding et al.
(Continued)

FOREIGN PATENT DOCUMENTS

DE    10054632    5/2002
JP    61-139755   8/1986
(Continued)

OTHER PUBLICATIONS

Installation and use manual, "HydropHobic cartridge and disposable Filters" Entergris, Jan. 31, 2011.
(Continued)

*Primary Examiner* — Lore R Jarrett
(74) *Attorney, Agent, or Firm* — Lex IP Meister, PLLC (57) ABSTRACT

A particle filtering device which shortens the separation time of particles and increases the separation efficiency are provided. The particle filtering device comprises: a filtration membrane which separates a particle by filtering a sample; a first body connected to an inlet side of the filtration membrane, which supplies the sample to the inlet side of the filtration membrane; and a second body connected to an outlet side of the filtration membrane, which accommodates a permeate whose particle is separated through the filtration membrane, wherein the particle filtering device has a structure in which the permeate is accommodated in advance (Continued)

between the second body and the outlet side of the filtration membrane.

13 Claims, 11 Drawing Sheets

(58) Field of Classification Search
CPC .......... B01L 2300/0681; C12N 5/0694; C12M 47/02; C12M 47/04; C12M 23/02; C12M 33/14
See application file for complete search history.

(56) References Cited

U.S. PATENT DOCUMENTS

| | | | |
|---|---|---|---|
| 5,301,685 | A | 4/1994 | Guirguis |
| 5,507,959 | A | 4/1996 | Glick |
| 2008/0056949 | A1 | 3/2008 | Lee |
| 2009/0176899 | A1* | 7/2009 | Yoo .................. B01L 3/502707 521/50.5 |
| 2013/0171697 | A1 | 7/2013 | Park et al. |

FOREIGN PATENT DOCUMENTS

| | | |
|---|---|---|
| JP | 64-052509 | 3/1989 |
| JP | 07-500910 | 1/1995 |
| JP | 07-022699 | 4/1995 |
| JP | 07-289858 | 11/1995 |
| JP | 08-501727 | 2/1996 |
| JP | 08-175999 | 7/1996 |
| JP | 2000-083649 | 3/2000 |
| JP | 2000-189405 | 7/2000 |
| JP | 2007-089566 | 4/2007 |
| JP | 2010-540927 | 12/2010 |
| JP | 2014-524242 | 9/2014 |
| KR | 10-2012-0042515 | 5/2012 |
| KR | 10-2012-0117834 | 10/2012 |
| KR | 10-2013-0127513 | 11/2013 |
| KR | 10-2014-0071222 | 6/2014 |
| WO | 2001-087486 | 11/2001 |
| WO | 2011-041671 | 4/2011 |
| WO | 2011/041671 | 4/2011 |

OTHER PUBLICATIONS

EPO, the search report, European Patent Application No. 15801307.8, Mar. 30, 2017.
Entergris, Inc., "Hydrophobic cartridge and disposable filters", Installation and use manual, Jun. 29, 2011.
Gaborski, Thomas R. et al., "High performance separation of nanoparticles with ultrathin porous nanocrystalline silicon membranes", ACS Nano, Nov. 23, 2010, vol. 4, No. 11, p. 6973-6981.
Kochan, J et al., "Impact of wetting agents on the filtration performance of polymeric ultrafiltration membranes", Desalination, 2009, vol. 241, p. 34-42
Ada Lee et al., "All-in-One Centrifugal Microfluidic Device for Size-Selective Circulating Tumor Cell Isolation with High Purity", Analytical Chemistry, vol. 86, p. 11349-11356, Oct. 15, 2014.

* cited by examiner

PARTICLE FILTERING DEVICE AND METHOD

FIELD OF THE INVENTION

The present invention relates to a particle filtering device and a method.

DESCRIPTION OF THE RELATED ART

Generally, separating a particle as the technology applied to various industries is separating a certain size of solid contained in the sample such as the liquid. In particular, a filtration is the technology which passes a filtered fluid by applying a pressure difference to both sides of the filter media and deposits a particle larger than the pores of the filter media to the surface of the media. The filtration can be easily applied, in addition, it needs to less energy consumption and less space, thus the filtration is utilized in the overall fields such as medical, chemical, environmental, food industries, or the likes.

For example, study cases which separates a biological sample by utilizing the filtration technology and performs a variety of biochemical tests by using the biological sample have been reported.

In a biological fluid of patients with the disease, there are biological particles which can be an indicator of various diseases as well as basic blood cells. By optionally separating and detecting such biomolecules, the patient's condition can be diagnosed, and the results can be used in personalized treatment.

Among them, a cancer diagnosis by using the selective separation of the circulating tumor cell (hereinafter referred to as CTC) is a typical example. CTC as a cancer cell distributed in the blood of metastatic cancer patients is a cell which plays a key role in causing the cancer metastasis because the CTC moves along the blood flow after going away from the original cancer tissue and penetrates into other issues. The number of CTC existing in the blood of the patient is known to be closely related with the progress of the cancer. Thus, counting the number by capturing the CTC can be an important biomarker which can monitor the progress of the cancer.

However, the number of CTC is very slim at a rate of one blood cell per 1 billion blood cells compared with other blood cells existing in the blood. Therefore, a very precise and accurate cell separation technique is required so that the CTC is utilized as the important biomarker.

Most of CTC separation methods currently known to date is a method which utilizes an antibody specifically bound to biomolecules expressed on the surface of the CTC. According to the method, CTC are coupled to a magnetic bead surface or a measurement surface by coating the antibody to the magnetic bead surface of the measurement surface and by flowing the blood therein. However, the case reporting that there is a limitation because the conventional structures stated above have various type of biomolecules expressed on the surface of the CTC and those amounts are non-uniformed.

To overcome the limitations noted above, the example that combines a separation method according to the physical characteristics of the cell on the microchip is introduced. For example, a typical prior art document related to the technology for capturing and detecting cells based on the size difference between cancer cells and blood cells is the Korean Patent Application Publication NO. 10-2012-0117834. Specifically, the technology related to a filtration system comprising a filtration module for the separation of cells or the target biological particles and a cell filtering method using the same are disclosed.

CONTENTS OF THE INVENTION

Problem to be Solved

A particle filtering device and method, which shortens the separation time of particles and increases the separation efficiency are provided.

Means for Solving Problem

A particle filtering device of the present embodiment, comprising: a filtration membrane which separates a particle by filtering a sample; a first body connected to an inlet side of the filtration membrane, which supplies the sample to the inlet side of the filtration membrane; and a second body connected to an outlet side of the filtration membrane, which accommodates a permeate whose particle is separated through the filtration membrane, wherein the particle filtering device may have a structure in which the permeate is accommodated in advance between the second body and the outlet side of the filtration membrane.

The permeate accommodated in advance between the second body and the outlet side of the filtration membrane may be accommodated in contact with the outlet side of the filtration membrane.

The permeate may be a solution with the same ingredients as the filtrate passed through the filtration membrane.

The first body may include: an inlet space formed at a position corresponding to the inlet side of the filtration membrane, in which the sample is introduced; an injection port for the sample injection, which is connected with the inlet space; and a guide member which transports the sample by connecting the injection port and the inlet space.

The particle filtering device may comprise a sample space which accommodates the sample injected from the injection port by being formed between the first body and the second body, by being connected with the guide member, and by being communicated with the injection port.

The second body may include an outlet space formed at a position corresponding to the outlet side of the filtration membrane, which accommodates the permeate.

The particle filtering device may further comprise a filtrate storage member which stores a filtrate passed through the filtration membrane by being formed between the first body and the second body and by being connected to the outlet space.

The second body may have a flow channel which connects the outlet space and the filtrate storage member.

The first body may further have a vent connected with the guide member.

The first body and the second body are formed as a disk-shaped structure to be rotatable around the center, and the filtration membrane may be located apart from the center of the second body in the radial direction.

The injection port may be located between the center of the first body and the filtration membrane.

The guide member may be formed so that the width of the guide member is gradually narrowed in the radial direction from the sample space to the inlet space along the direction of movement of the sample.

The filtration membrane may be a structure which has pores whose diameter is 10 nm to 30 cm.

The filtration membrane may be a structure which filters a living cell, an inorganic material particle, or an organic material particle.

A particle filtering method of the present embodiment, which may comprise: injecting the permeate to the outlet space of the particle filtering device; injecting the sample to the particle filtering device; guiding the sample to the filtration membrane of the particle filtering device by generating the centrifugal force; and separating the particle by filtering the sample through the filtration membrane.

Effects of the Invention

According to an embodiment of the present invention as described above, the front surface of the outlet side of the filtration membrane is contacted in advance by the permeate before filtering the sample, thus the sample can more quickly and easily passes through the pores of the filtration membrane even though the capillary pressure is greater due to the small pores of the filtration membrane. Thus, the time required for the particle separation is possible to be reduced.

In addition, filtering the sample can be performed even in a lower pressure.

Furthermore, as the sample evenly passes through the filtration membrane over the entire surface of the filtration membrane, the available area of the filtration membrane is maximally expanded. Thus, it is possible to increase the filtering efficiency.

Moreover, the separated particle can be prepared in the form of a detection solution by directly dyeing the separated particle in the body or by dissolving, thus the present invention can detect the particle without dismantling the body.

DETAILED DESCRIPTION

The terminology used below are merely to refer to a particular embodiment and are not intended to limit the present invention. As used herein, the singular forms also include the plural forms unless the context clearly indicates otherwise. Further, in this specification, the term said that "a certain part comprises a certain component" means not the exclusion of other components but the inclusion of other components unless it is specifically described to the contrary. Moreover, the size and thickness of each configuration shown in the drawings are arbitrarily shown for convenience to explain, so the present invention is not necessarily limited by illustration.

Hereinafter, with reference to the attached drawings, embodiments of the present invention will be described so that a person ordinarily skilled in the art can readily conduct. As can be readily appreciated by the person ordinarily skilled in the art, embodiments described below can be modified in various forms to the extent not departing from the spirit and scope of the invention. Thus, the present invention can be implemented in many different forms and should not be limited to the embodiments set forth herein.

Hereinafter, in the present invention, "on" means that it is located on or below the target member, and it does not necessarily mean that it is located on the target member based on the gravity direction.

Hereinafter, the present embodiment describes a case of filter-separating the circulating tumor cell (CTC) as a rare tumor cell contained in a biological sample by using the whole blood containing the rare tumor cell particle as the biological sample which separates the particle. The present invention is not limited to the following embodiment, and it would be applicable to any technology which separates particles from the various samples by the filtration method.

Figure 1:
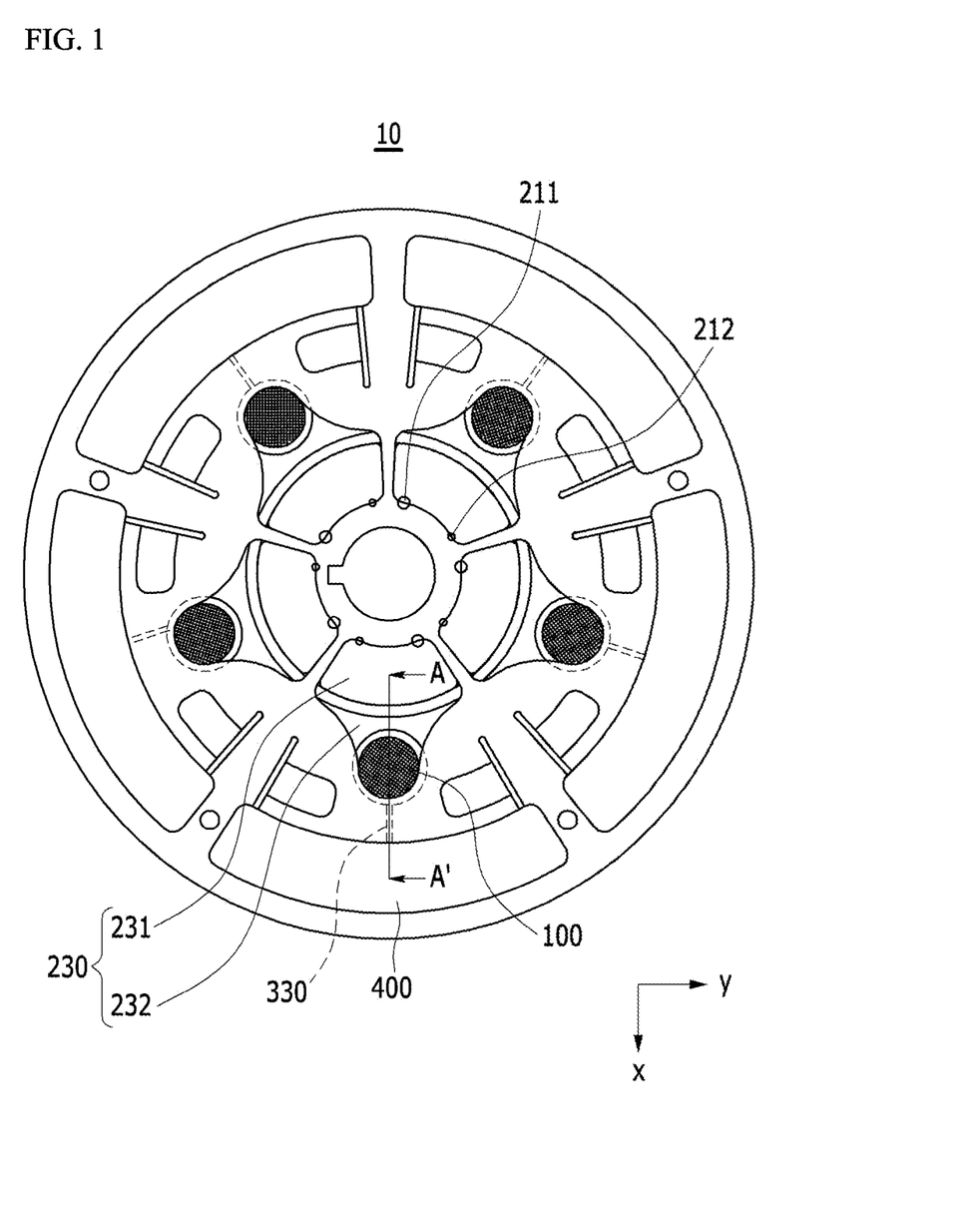
FIG. 1 is a view showing a particle filtering device according to this embodiment.
Figure 2:
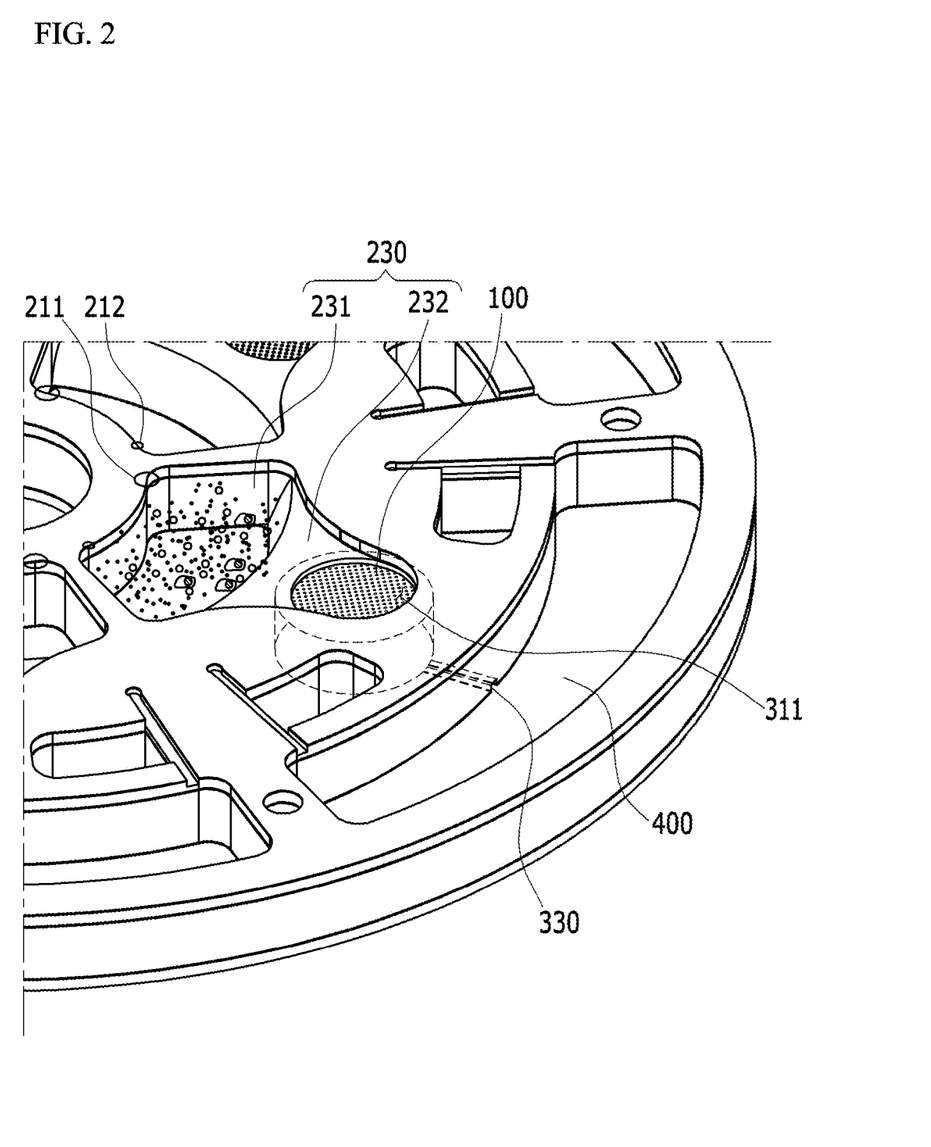
FIG. 2 is a perspective view of a particle filtering device according to this embodiment.
Figure 3:
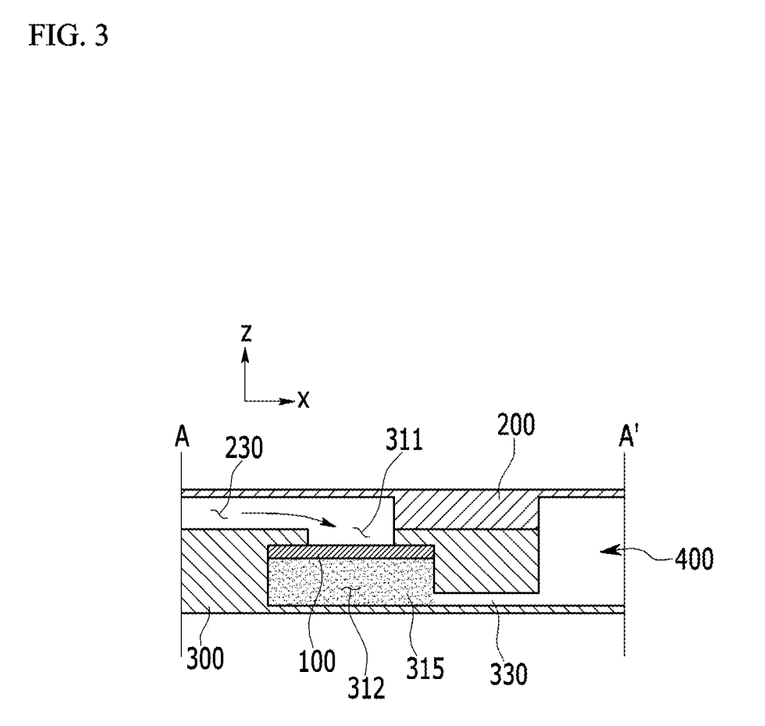
FIG. 3 is a cross-sectional view of the A-A' section in FIG. 1.

FIG. 1 and FIG. 2 show the appearance of the particle filtering device according to this embodiment, and FIG. 3 shows the cross-section of A-A' line of FIG. 1.

A particle filtering device (10) according to this embodiment comprises: a filtration membrane (100) which filters a biological sample; a first body (200) located on the filtration membrane (100); and a second body (300) connected with the filtration membrane (100) and coupled to the lower portion of the first body (200).

The first body (200) supplies the biological sample to the inlet side of the filtration membrane by connecting to the inlet side of the filtration membrane (100). Further, the second body (300) connected to the outlet side of the filtration membrane (100) accommodates a filtrate whose particle is separated through the filtration membrane.

The particle filtering device in this embodiment has a structure in which the permeate is accommodated in advance between the second body and the outlet side of the filtration membrane (referred to as 315 in FIG. 3). As a result, the sample introduced to the inlet side of the filtration membrane can easily pass through fine pores of the filtration membrane even under the smaller pressure. Therefore, it is possible to more quickly separate the particle by filtering the sample. This will be described in detail later.

Here, the inlet side of the filtration membrane means a side to which the biological sample is contacted, wherein the entrance of the pores formed in the filtration membrane is positioned among the both sides of the filtration membrane. The outlet side of the filtration membrane means a side as the opposite side of the inlet side, in which the outlet of pores formed in the filtration membrane is located. In the present embodiment, as described in FIG. 3, the upper surface of the filtration membrane forms the inlet side along the z-axis direction, so the first body is located on the filtration membrane. The lower surface forms the outlet side, thus the second body is located under the filtration membrane. Furthermore, the biological sample or the sample means the state containing the particles, and the permeate means the solution in which the particles are separated as the biological sample or the sample passes through the filtration membrane.

The filtration membrane (100) has a number of pores to separate the particles, in particular, the various sizes of the pores of 3 nm to 30 cm may be formed to separate particles with various sizes. In the present embodiment, the filtration membrane (100) may have the pores whose diameter of 5 to 10 μm to capture the circulating tumor cell existing in the whole blood sample. However, as it contains an error that may occur when attaching the filtration membrane (100) to the second body (300), the diameter of the fine pores is not necessarily limited to thereto. Thus, the diameter may be formed in various ways depending on the size of the particles to be separated.

The filtration membrane (100) may be formed by a variety of materials to filter the living cell, the inorganic material particle, an organic material particle, or the like. For example, the filtration membrane (100) may be formed by the biologically inert material to be applied to the biological sample. The filtration membrane may be formed by the material having the optical transmittance at the same time. Thus, a rare cell may be detected by using an optical detector without separating the filtration membrane (100) from the second body (300).

The filtration membrane (100) may be formed by the same material of the second body (300) to facilitate adhesion with the second body (300). For example, when both the second body (300) and the filtration membrane (100) are formed by a polycarbonate material, the filtration membrane (100) may be bonded to the second body (300) by chemically dissolving the bonding area by administration of a small amount of acetone to the edge area in which the second body (300) and the filtration membrane (100) are coupled. Accordingly, it is possible to prevent wrinkles caused from the installation of the filtration membrane (100) in the second body (300) and leakage of the rare cell caused from the incomplete installation of the filtration membrane (100) in the second body (300).

However, a bonding method between the filtration membrane and the second body is not necessarily limited to the chemical bonding method, and the filtration membrane (100) may be irreversibly bonded to the second body (300) through a variety of bonding methods such as a thermal bonding, an UV resin bonding, an ultrasonic bonding, or the like.

The first body (200) and the second body (300) may be formed as a disk-shaped structure to be rotatable around the center. The particle filtering device (10) according to the present embodiment may be a disk structure in which the first body (200) and the second body (300) are sequentially stacked.

The filtration membrane (100) may be located by being located apart from the center of the second body (200). The first body (200) and the second body (300) may be formed to have the same diameter.

Moreover, the particle filtering device (10) in the present embodiment may have a hollow passing through the center of the first body (200) and the second body (300) to install the rotation axis in the center of the particle filtering device (10).

The surface of the first body (200) and the second body (300) may be a biologically inert material which also has the optical transmittance, for example, polystyrene (PS), poly dimethyl siloxane (PDMS), poly methylmethacrylate, (PMMA), polyacrylate, polycarbonate, polycyclic olefins, polyimide, polyurethanes, or the like.

Thus, the biological stability can be secured because the biological sample does not react with the first body (200) and the second body (300) when the biological sample is injected in the first body (200), furthermore, the separated rare cell can be detected by being passed through the first body (200) and the second body (200) by using an optical detector without discharging the separated rare cell toward the outside of the particle filtering device (10).

The first body (200) includes: an inlet space (311) formed at a position corresponding to the inlet side of the filtration membrane (100), in which the biological sample is introduced; an injection port (211) for the sample injection, which is connected with the inlet space (311); and a guide member (230) which transports the sample by connecting the injection port and the inlet space.

The injection port (211) may be formed by passing through the first body (200). Thus, the biological sample for separating the rare cell may be injected in the first body (200) through the injection port (211). Furthermore, multiple injection ports (211), as shown in FIG. 2, may be formed at intervals along the circumferential direction based on the center of the first body (200). As a result, the biological sample can be injected from various directions of the first body (200).

The injection port (211) may be located between the center of the first body (200) and the filtration membrane (100). Thus, the biological sample injected by the injection port (211) can be easily moved to the filtration membrane (100) through the centrifugal force during the rotation of the first body (200) and the second body (300).

In the first body (200), a vent as well as the injection port (211) may be formed. The vent (212) may be formed by passing through the first body (200). At this time, as shown in FIG. 1, the vent (212) may be formed on the first body (200) so as to be adjacent to the injection port (211). Thus, during the injection of the biological sample to the injection port (211) the air existing in the body (200) can be smoothly discharged to the outside.

In the first body (200), a guide member (230) connected with the injection port (211) may be formed. The guide member (230) connects between the injection port (211) and the inlet space (311) existing on the filtration membrane. The guide member (230) guides the biological sample which is injected in the first body (200) through the injection port (211) to the inlet side of the filtration membrane (100) by moving the biological sample to the inlet space.

Multiple guide members (230) may be formed at intervals along the circumferential direction of the first body (200). Moreover, the guide member (230) may be formed in the opposite direction of the center of the first body (200) based on the injection port (211) as described in FIG. 2. Thus, the biological sample can be more rapidly guided in the radial direction of the first body (200) through the centrifugal force during the rotation of the particle filtering device (10).

The inside of the first body (200) has a sample space which accommodates the biological sample injected in the first body though the injection port (211)

In the present embodiment, the sample space is a biological sample containing space connected with the guide member.

For this purpose, the guide member (230) includes a first part (231) which functions to the sample space and a second part (232) which functions to the biological sample flow channel. Thus, the biological sample injected by the injection port (211) is accommodated in the first part (231)

forming the sample space, and the biological sample is moved through the second part (232) connected with the first part (231).

As shown in FIG. 1 and FIG. 2, the first part (231) may be formed so that the width of the first part (231) is gradually widened in the radical direction of the first body (200) based on the center of the first body (200). Thus, the fluid resistance of the biological sample introduced to the first part (231) through the injection port (211) can be minimized. The cross-section of the first part (231) is formed in an arc shape around the center of the first body (200), but it is not necessarily limited to this shape.

The second part (232) is formed by connecting to a first part, wherein the width of the first part (231) may be gradually narrowed from the end of the first part (231) to the outward of the first body (200) in a radial direction around the center of the first body (200). Thus, the biological sample introduced to the second part (232) through the first part (231) is easily collected in the outward of the second part (232) around the center of the first body (200).

The biological sample moved to the outward of the second part (232) is moved to the inlet space (311) connected with the outward of the second part. The inlet space (311) can be understood as a space connected with the second part and formed on the inlet side of the filtration membrane (100).

The biological sample moved through the second part (232) is accommodated in the inlet space (311) and the biological sample contacts with the front of the inlet side of the filtration membrane. The biological sample introduced in the inlet space (311) is filtered through the filtration membrane along the direction of arrow in FIG. 3.

The filtrate passed though the filtration membrane (100) is moved to the outlet space (312) located in the outlet side of the filtration membrane (100).

Figure 4:
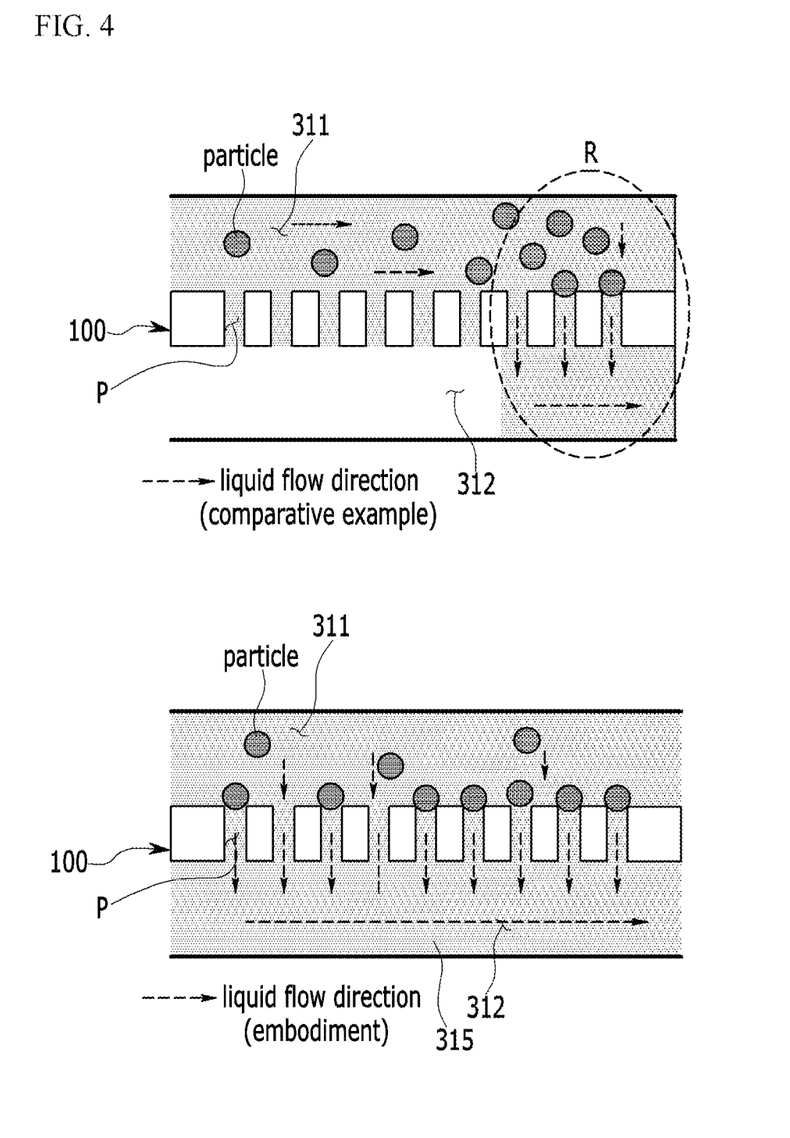
FIG. 4 is a schematic view for explaining the operation of a particle filtering device according to this embodiment.

As shown in FIG. 4, the second body (300) has the outlet space (312) in which the permeate passed through the filtration membrane is accommodated, and the outlet space is located at a position corresponding to the outlet side of the filtration membrane. The outlet space (312) can be understood as a space formed under the outlet side of the filtration membrane in the second body (300).

The particle filtering device (10) of the present embodiment is a structure in which the permeate is accommodated in advance in the outlet space (312) before filtering the biological sample.

The permeate (315) may be the same solution with the conditions in which the particle is separated from the biological sample. It means that the permeate may be the same solution with the filtrate filtered through the filtration membrane. Moreover, any solution can be applied as the permeate if the solution does not have a separating target particle, and does not affect the biological sample or the permeate, and can reduce the capillary pressure of the pores of the filtration membrane in the outlet side of the filtration membrane.

For example, when assembling the first body and the second body, the permeate (315) can be accommodated in the outlet space of the second body in advance to prepare the particle filtering device. Further, the permeate is injected in the outlet space through the injection port after preparing the particle filtering device by connecting with the outlet space in the second body and forming an additional injection port capable of opening and closing.

The permeate (315) accommodated in the outlet space (312) in advance may be accommodated in contact with the outlet side of the filtration membrane (100). Thus, the entire outlet side of the filtration membrane is faced with the permeate because the permeate is filled in the outlet space. In addition to the above described structure, the permeate is not faced to the outlet side of the filtration membrane because only some of the permeate is accommodated in the outlet space. In the case of this structure, it is possible to obtain the same effects by contacting the permeate accommodated in the outlet space to the entire outlet side of the filtration membrane by shaking the particle filtering device as necessary or use.

FIG. 4 is a schematic view for explaining the operation effects of the permeate according to this embodiment.

As shown in FIG. 4, if the permeate (315) which has not particles is filled in the outlet space (312) faced to the outlet side of the filtration membrane (100), the permeate acts as a priming water against the pores (P) of the filtration membrane.

The particle separation which uses the filtration membrane performs a filtration basically by using the pressure difference between both sides of the filtration membrane. During the filtration, the solution existing in the sample passes through the pores of the filtration membrane, and the particles larger than the pores are deposited on the surface of the inlet side of the filtration membrane since the particles cannot pass through the pores of the filtration membrane.

For the solution existing in the sample passes through the pores of the filtration membrane, the capillary pressure related to the surface tension is overcame in the outlet of the pores. Such capillary pressure is proportional to the surface tension, and the capillary pressure is inversely proportional to the size of the pores. Thus, if the filtration process uses the filtration membrane having the very small pores, the very large pressure is required for passing of the solution existing in the sample through the pores.

The comparative example of the FIG. 4 does not use the principle of the priming water, and the comparative example describes the state in which the sample is filtered without the permeate in the outlet space located in the outlet side of the filtration membrane.

In the state without the permeate as the comparative example, the solution in the sample introduced in the inlet side of the filtration membrane (100) does not pass through the pores due to the capillary pressure taken in the pores (P) of the filtration membrane. Furthermore, if the solution flows between the pores of the certain part (R) by overcoming the force of the capillary, the solution is filtered only to the certain part (R). Thus, the fluid flow resistance is significantly reduced in the particular part in which the solution flows. As a result, the sample continues to flow only in the particular part, and the filtration is performed in this part. Therefore, a particle separation is performed in only the particular part in which the solution flows. As a result, in case of the comparative example, the filtration is not performed in the front of the filtration membrane. In addition, only the area of the certain part (R) can be used to separate the particles.

Since the entire area of the filtration membrane is not used to the filtration, it takes a lot of time for the filtration and the filtration efficiency is degraded.

As mentioned above, the example of the FIG. 4, which uses the principle of the priming water and describes the state in which the sample is filtered by filling in advance the permeate to the outlet space (312) of the outlet side of the filtration membrane.

As the example, when the permeate (315) is filled in the outlet space (312) of the filtration membrane (100), the outlet side of the filtration membrane become in contact to the permeate. In this state, the solution existing in the sample, which is introduced to the inlet side of the filtration membrane, smoothly flows by directly passing through the pores without overcoming the force of the capillary by the cohesive force of the permeate (315) contacted to the outlet of pores (P) of the filtration membrane. The permeate contacts to the front of the outlet side of the filtration membrane, so the solution existing in the sample flows and passes through the pores in the front of the inlet side of the filtration membrane.

As a result, the filtration is performed because the solution existing in the sample passes through the pores with the smaller flow resistance in the front of the filtration membrane (100). Since the filtration is performed in the front of the filtration membrane, the entire filtration membrane can be used for the filtration. Thus, the filtration time and the filtration efficiency can be highly improved. Furthermore, although the pores of the filtration membrane is small, the filtration can be performed by the smaller pressure.

A particle filtering device of the present embodiment, which is formed between the first body (200) and the second body (300), may comprise the filtrate storage member (400) which stores a filtrate passed through the filtration membrane (100). The filtrate storage member (400) may be a space located in the particle filtering device (10) formed between the first body (200) and the second body (300) by the combination of the first body (200) and the second body (300), but it is not necessarily to be limited to this configuration.

The filtrate storage member (400) is formed in the opposite direction of the center of the first body (200) based on the filtration membrane (100). As shown in FIG. 1, the filtrate storage member (400) may be formed in an arc shape with multiple pieces in the particle filtering device (10).

At this time, the filtrate passed through the filtration membrane (100) can be supplied to the filtrate storage member (400) because the flow channel is formed between the outlet space (311) and the filtrate storage member (400). Each width and height of the fluid channel (330) is formed in 1 mm or less to pass the filtrate therein and to prevent the filtrate from reversing flow in the filtration membrane (100) direction, but it is not necessarily limited to such value.

Figure 5:
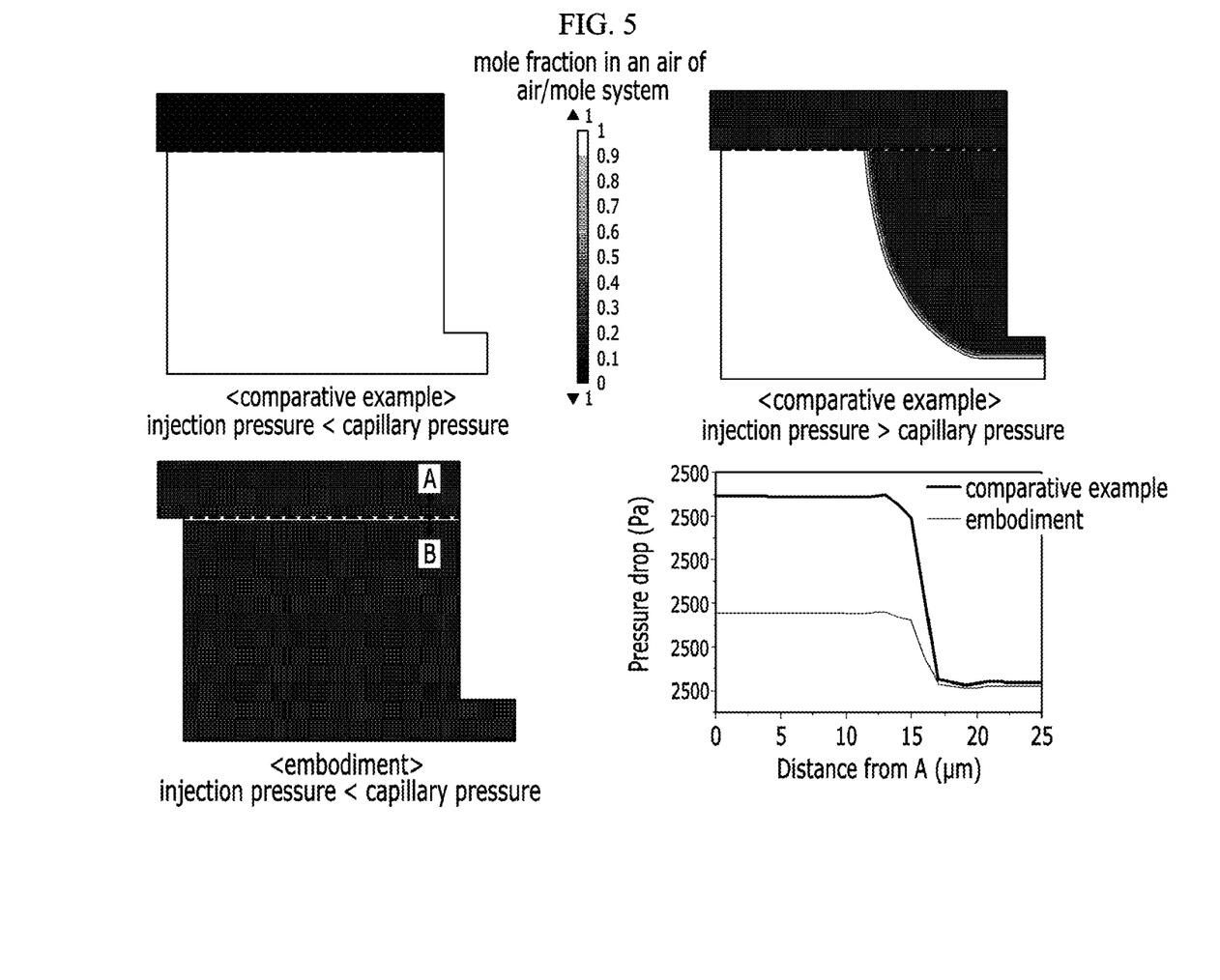
FIG. 5 is a view showing the simulation results of the flow of the solution which is closed to a filtration membrane of a particle filtering device according to this embodiment.

FIG. 5 indicates the simulation results of the flow of the solution which is closed to the filtration membrane in accordance with the presence or absence of the utilizing the principle of priming water according to this embodiment.

The embodiment of the FIG. 5 is the simulation results of the flow of the solution after filling the permeate to the outlet side of the filtration membrane by applying the principle of the priming water. The comparative example is the simulation results of the flow of the solution in the state without the permeate in the outlet side of the filtration membrane because the principle of the priming water is not applied thereto.

In case of the comparative example, when a constant pressure is applied through the injection port, the solution fills the inlet space and is subjected to the force of the capillary in the pore outlet of the filtration membrane. When the pressure applied from the injection port is smaller than the force of the capillary, the solution is trapped and is not flow because the pores of the filtration membrane does not overcome. When applying the pressure greater than the force of the capillary to the injection port to overcome the pores, the solution flows through the part of the pore portions in the filtration membrane. Thus, it can be shown that the solution flows only through the flow passage.

However, if the priming water is present in the outlet space as in the embodiment, the solution existing in the outlet space is possible to flow in contact with the priming water without overcoming the force of the capillary in the pore outlet. Therefore, the solution can flow under much lower pressure.

In addition, as in the graph of FIG. 5, the calculation results of the pressure difference between before and after passing through the filtration membrane when the solution flows indicates that a greater pressure difference is present due to the low flow area when the solution flows through the part of the filtration membrane without the priming water as the comparative example. This may interfere with the stability at the time of filtering the biological material. In contrast, when applying the priming water as shown in the embodiment, the solution can flow at much lower pressure difference through the full-scale of the filtration membrane and perform the stable filtration of material.

The above described the configuration of the particle filtering device (10) according to the first embodiment of the present invention. Hereinafter will be explained the particle filtering method which uses the particle filtering device (10) according to the first embodiment of the present invention.

Figure 6:
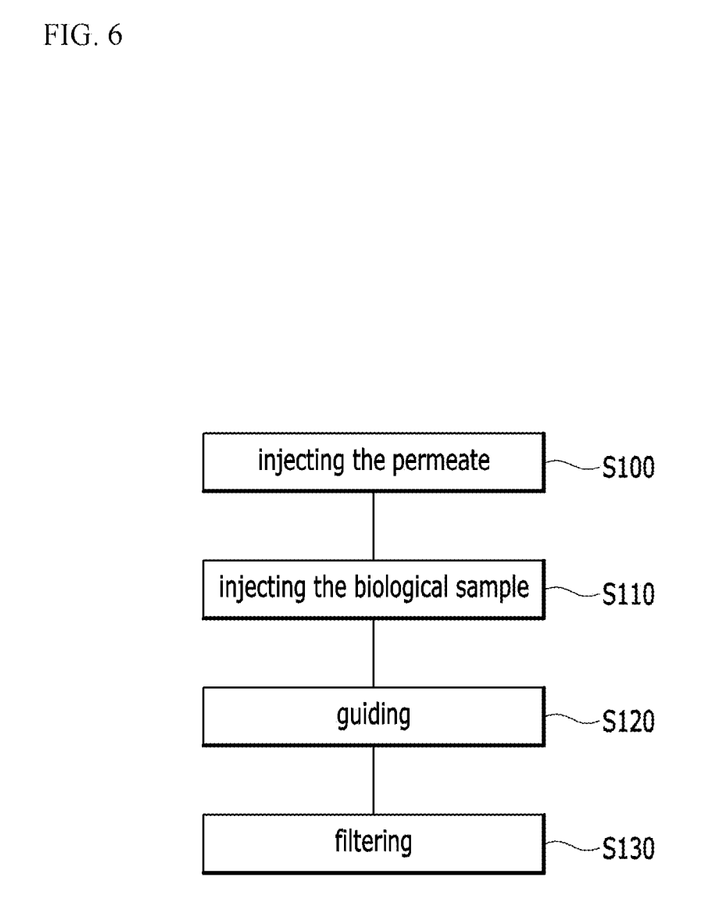
FIG. 6 is a flow chart showing a particle separation method according to this embodiment.

FIG. 6 is a flow chart showing a particle filtering method which uses the particle filtering device according to the embodiment.

Referring to FIG. 6, the particle filtering method which uses the particle filtering device (10) according to the embodiment may comprise: pre-injecting the permeate to the outlet space of the particle filtering device (S100); injecting the biological sample to the inside of the particle filtering device (S110); guiding the biological sample to the filtration membrane (100) by generating the centrifugal force (S120); and separating the particle by filtering the biological sample through the filtration membrane (100) (S130).

In the injecting the permeate (S100), the permeate is injected in the outlet space faced to the outlet side of the filtration membrane before filtering the sample. In this embodiment, the whole blood sample in which the circulating tumor cell included is used as the biological sample, so the particle of the circulating tumor cell is separated through the filtration membrane. Thus, the permeate may be a solution with the state in which the circulating tumor cell is removed from the whole blood sample. The permeate is faced with the outlet side of the filtration membrane.

In the injecting the biological sample (S110), the biological sample is injected in the particle filtering device (10) through the injection port (211). The injected biological sample is present with the state in which the circulating tumor cell is included in the guide member (230).

In the guiding (S120), the biological sample existing in the guide member (230) is guided to the filtration membrane (100). At this time, in this embodiment, the centrifugal force can be generated by rotating the particle filtering device (10) for rapid guidance of the biological sample. By the method as described above, the biological sample is located in the inlet space of the upper filtration membrane.

In the filtering (S130), the biological sample introduced to the filtration membrane (100) is filtered. The filtration is performed by the biological sample which passes through the filtration membrane by the pressure difference between the inlet side and the outlet side of the filtration membrane. At this time, the circulating tumor cell whose molecular size is large remains in the inlet side of the filtration membrane since the cell does not pass through the pores of the filtration membrane (100). The rest can pass through the pores of the filtration membrane and is moved to the outlet space located in the outlet side of the filtration membrane.

In this process, the permeate pre-filled in the outlet space applies the cohesive force to the sample in the pore outlet of the filtration membrane, thus the sample easily can pass through the pores of the filtration membrane without overcoming the capillary force. The filtrate which passes through the filtration membrane in the filtering moves to the filtrate storage member (400) via the flow channel (330).

Experimental Example 1

Figure 7:
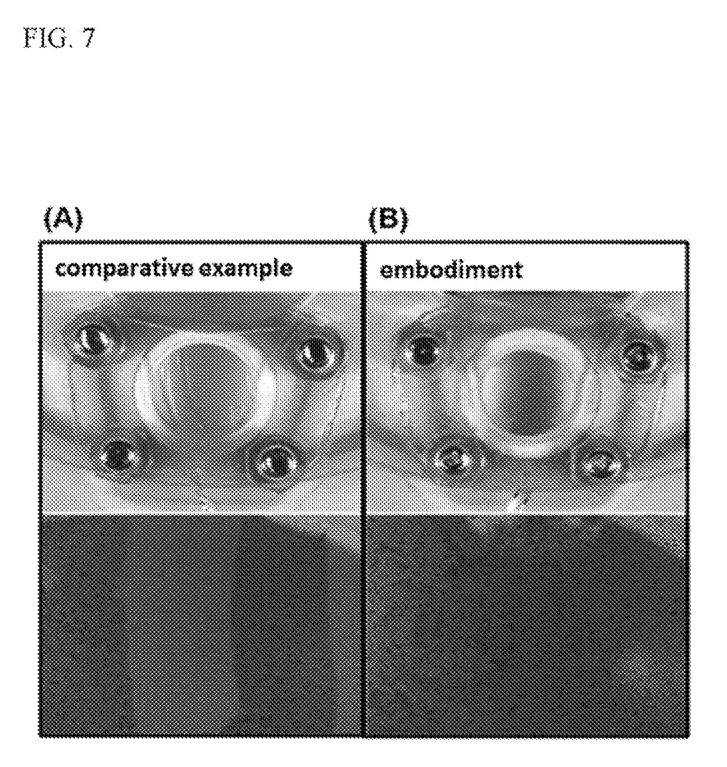
FIG. 7 is a photo showing the experimental result of a particle separation of a particle filtering device according to this embodiment.

FIG. 7 is a photo comparably showing the experimental result of the particle separation of the particle filtering device according to this embodiment.

In this experiment, the filtration is performed by injecting the permeate including particles of 10 μm as the sample to the particle filtering device having the filtration membrane whose pore size of 8 μm.

In FIG. 7, both the comparative example and the embodiment have the same structure of the particle filtering device, but merely in the embodiment, the permeate is pre-injected to the outlet space of the outlet side of the filtration membrane, on the contrary, the comparative example has no permeate.

As indicated in the photo of the comparative example of FIG. 7, the filtration is performed without applying the principle of the priming water by the permeate, as a result, only certain parts of the filtration membrane can be used for the filtration. Thus, as seen by expanding the filtration membrane, it can be seen that the particles are deposited in only part in which the solution flows like a stream.

The embodiment of FIG. 7 shows the photo obtained when performing the filtration by applying the principle of the priming water by the permeate. In case of the embodiment, unlike the comparative example, the flow such as the stream is not formed in the specific part. The full-scale of the filtration membrane can be smoothly used for the filtration. As a result, it can be seen that the particles are uniformly deposited in the full-scale of the filtration membrane by enlarged observation of the filtration membrane.

Through these experiments, it can be known that the filtration is uniformly performed through the front of the filtration membrane if the permeate is pre-injected to the outlet side of the filtration membrane under the same structure of the particle filtering device.

Figure 8:
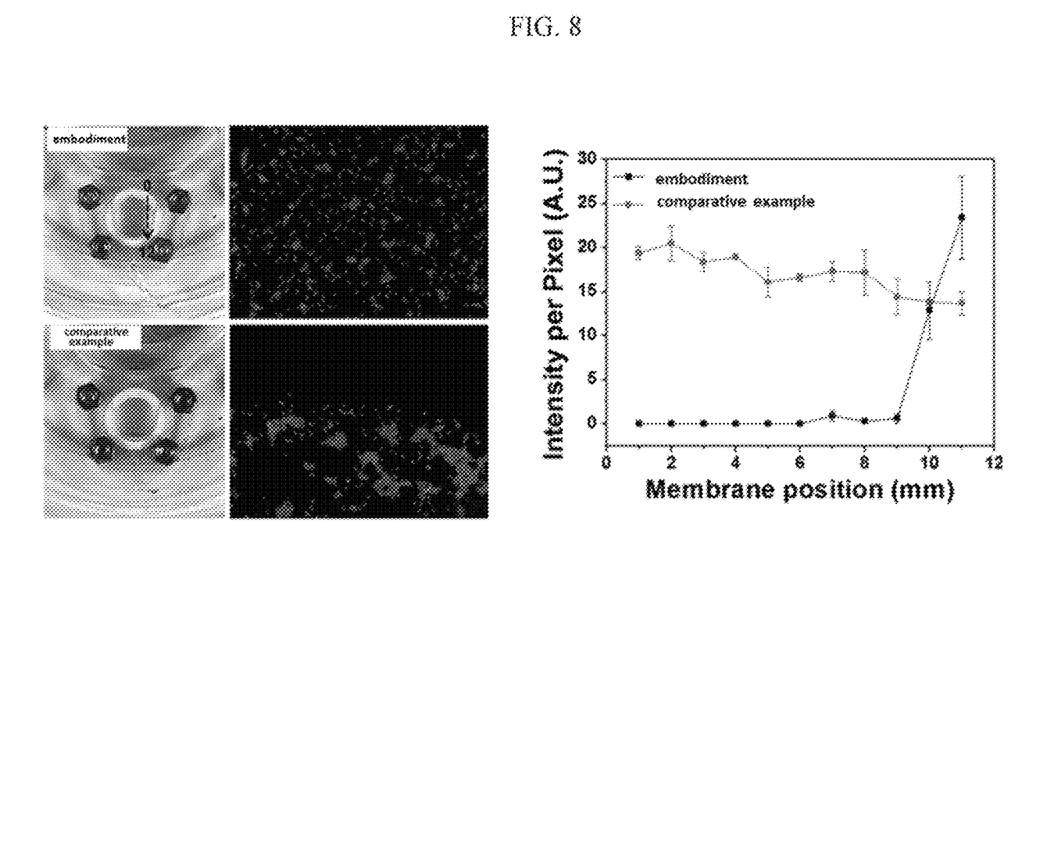
FIG. 8 is a view showing the experimental result of a fluorescent particle separation according to this embodiment.

FIG. 8 shows the experimental result of separating the actual fluorescent particle by using the principle of the priming water according to this embodiment.

In FIG. 8, both the comparative example and the embodiment have the same structure of the particle filtering device, but merely in the embodiment, the permeate is pre-injected to the outlet space of the outlet side of the filtration membrane, on the contrary, the comparative example has no permeate.

As the experimental result of separating the actual fluorescent particle, it can be known that the filtered particles are uniformly distributed in the full-scale because the solution is uniformly filtered through the full-scale under the filtration membrane which uses the principle of the priming water as in the embodiment. On the other hand, in case of filtering without the priming water as in the comparative example, it can be seen that only some parts of the lower portion are used for the filtration due to the fluid flow via the partial area of the filtration membrane. In the results after the particle filtration, it is possible to see the significant difference results in both the area used for the filtration and the area not used for the filtration.

Furthermore, as in the graph of FIG. 8, as a result of measuring the fluorescence intensity in each position with holding the upper part of the filtration membrane to zero, in case of the embodiment in which the principle of the priming water is applied the fluorescent intensity is uniformly distributed in the full-scale. On the other hand, in case of the comparative example in which the principle of the priming water is not applied, the fluorescent particles are intensively separated only in the lower portion of the filtration membrane.

Experimental Example 2

Figure 9:
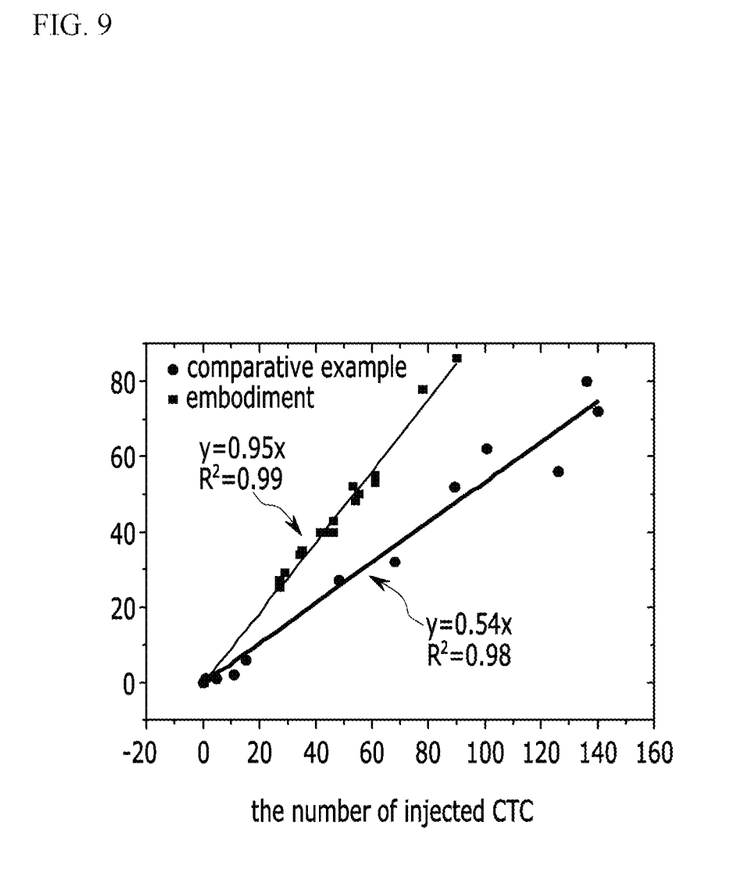
FIG. 9 and FIG. 10 are graphs showing the experimental result of a particle separation according to this embodiment.
Figure 10:
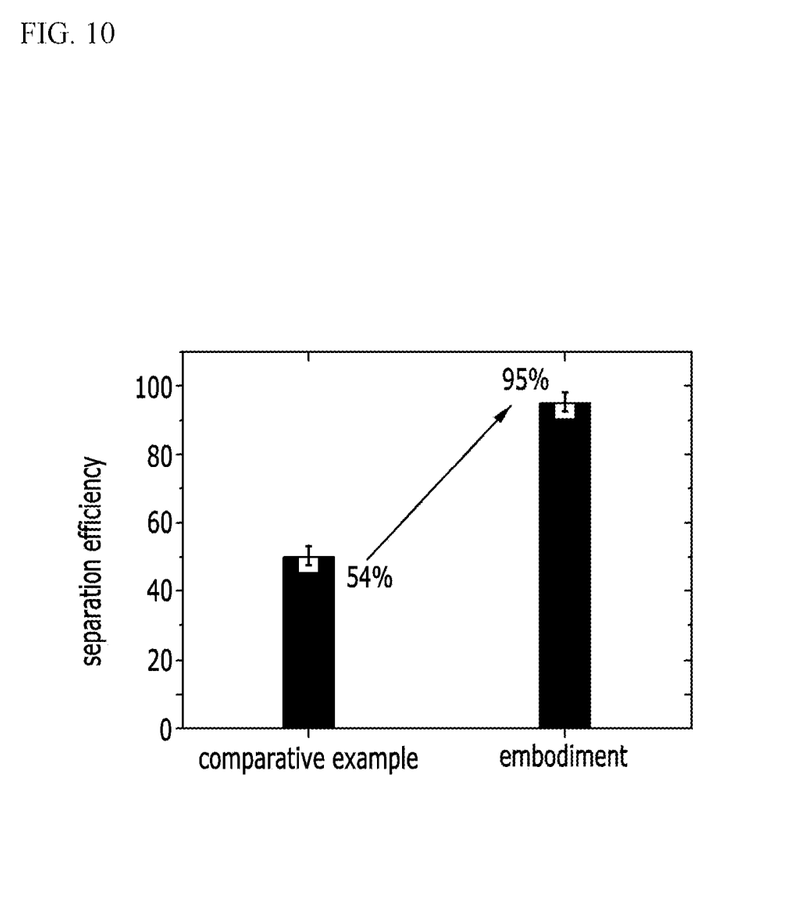

FIG. 9 and FIG. 10 are graphs indicating the experimental result of separating the CTC by the particle filtering device according to this embodiment.

FIG. 9 shows the correlation between the artificially injected CTC number and CTC number separated through the actual particle filtering device. FIG. 10 indicates the separation efficiency.

In FIG. 9 and FIG. 10, both the comparative example and the embodiment had the same structure of the particle filtering device, but merely in the embodiment, the permeate was pre-injected to the outlet space of the outlet side of the filtration membrane, on the contrary, the comparative example performed the CTC separation experiment without the permeate.

Both the comparative example and the embodiment performed the filtration by putting the number of CTC as artificially calculated into the sample and by injecting the sample to the particle filtering device. After the filtration, the number of CTC captured in the filtration membrane were aggregated and compared.

As shown in FIG. 9, the embodiment has much larger number of the captured CTC than that of the comparative example. Moreover, as shown in FIG. 10, the embodiment has much improved CTC separation efficiency of 95% when applied to the principle of priming water compared to that of the comparative example of 54%.

Figure 11:
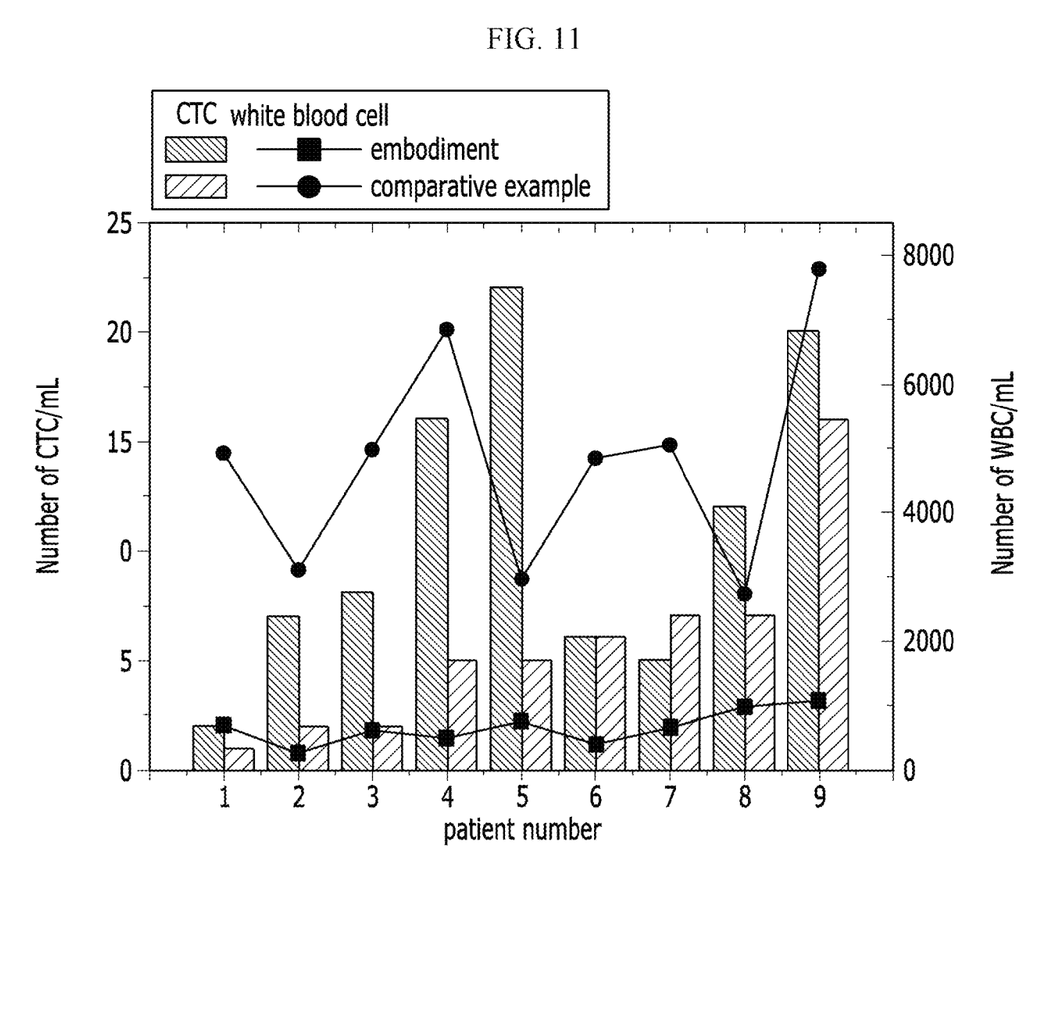
FIG. 11 is a graph showing the CTC separation result of the sample of the actual cancer patient, which uses a particle filtering device according to this embodiment.

FIG. 11 is a graph showing the CTC separation results of the sample of the actual cancer patient, which uses a particle filtering device according to this embodiment.

In FIG. 11, as described before, the embodiment indicates the separation result of the particle filtering device in which the principle of the priming water is applied. The comparative example shows the result of the CTC separation kit in which the principle of the priming water currently available is not applied.

As shown in FIG. 11, according to the experimental results of separation, more CTC were detected in the particle filtering device according to the embodiment than the particle filtering device according to the comparative example under the sample of the most of patients although the same patient sample were used therein. Thus, the embodiment utilizing the principle of the priming water can stably separate CTC in the wider area in comparison with the comparative example.

Moreover, a white blood cell which can act as an inhibitor should be removed as much as possible for the subsequent genetic diagnosis process after separation of CTC. In case of the embodiment, a much smaller number of white blood cell remains in the filter in comparison with the comparative example, therefore the embodiment has a high effect for removing the white blood cell.

Through these experiments, it can be known that the particle separation efficiency can be more increased if the permeate is pre-injected to the outlet side of the filtration membrane under the same structure of the particle filtering device.

Although the preferred embodiment of the present invention has been described above, the present invention is not limited thereto and can be performed by one of several variations within the claims, the description, and the accompanying drawings. It is also within the scope of the present invention.

| DESCRIPTION OF REFERENCE NUMERALS | |
|---|---|
| 10: particle filtering device | 100: filtration membrane |
| 200: first body | 211: injection port |
| 212: vent | 230: guide member |
| 231: first part | 232: second part |
| 300: second body | 311: inlet space |
| 312: outlet space | 315: permeate |
| 330: flow channel | 400: filtrate storage member |

What is claimed is:

1. A particle filtering device comprising:
a filtration membrane which separates a particle by filtering a sample;
a first body connected to an inlet side of the filtration membrane, wherein the first body supplies the sample to the inlet side of the filtration membrane, and includes an inlet space formed at a position corresponding to the inlet side of the filtration membrane, in which the sample is introduced;
a second body connected to an outlet side of the filtration membrane, wherein the second body receives a filtrate which is a filtrated solution of the sample by passing through the filtration membrane; and
a permeate accommodated in an outlet space of the second body formed to correspond to the outlet side of the filtration membrane, wherein the permeate is a same solution as the filtrate,
wherein the permeate is disposed in the outlet space of the second body and acts as a priming water against pores of the filtration membrane,
wherein the first body and the second body are formed as a disk-shaped structure to be rotatable around the center, and
wherein the outlet space is disposed under the inlet space via the filtration membrane along a perpendicular direction to a radial direction of the disk-shaped structure.

2. The device of claim 1,
wherein the first body further includes an injection port for the sample injection, which is connected with the inlet space; and a guide member which transports the sample by connecting the injection port and the inlet space.

3. The device of claim 2,
wherein the guide member comprises a first part which is formed between the first body and the second body, and communicated with the injection port to accommodate the sample injected from the injection port.

4. The device of claim 3,
wherein the particle filtering device further comprises a filtrate storage member which is formed between the first body and the second body and connected to the outlet space to store a filtrate passed through the filtration membrane.

5. The device of claim 4,
wherein the second body has a flow channel which connects the outlet space and the filtrate storage member.

6. The device of claim 5,
wherein the first body further has a vent connected with the guide member.

7. The device of claim 6,
wherein the filtration membrane is located apart from a center of the second body in a radial direction.

8. The device of claim 7,
wherein the injection port is located between a center of the first body and the filtration membrane.

9. The device of claim 8,
wherein the guide member is formed so that a width of the guide member is gradually narrowed in a radial direction from the first part to the inlet space along a direction of movement of the sample.

10. The device of claim 1,
wherein the permeate is accommodated in contact with the outlet side of the filtration membrane.

11. The device of claim 10,
wherein the filtration membrane has a pore having a diameter in a range of 10 nm to 30 cm.

12. The device of claim 11,
wherein the filtration membrane filters a living cell, an inorganic material particle, or an organic material particle.

13. A particle filtering method comprising:
a) injecting a permeate as a priming water to an outlet space of a particle filtering device;
b) contacting the permeate with a filtration membrane of the particle filtering device after step a);
c) injecting a sample to an inlet side of the particle filtering device after step b);
d) guiding the sample to the filtration membrane of the particle filtering device by generating a centrifugal force after step c); and
e) separating a particle from the sample by passing the sample through the filtration membrane to obtain a filtrate after step d),
wherein the permeate is a same solution as the filtrate passed through the filtration membrane.

* * * * *